(12) United States Patent
Bielski et al.

(10) Patent No.: US 7,783,009 B2
(45) Date of Patent: Aug. 24, 2010

(54) REDUNDANT SWITCH MECHANISM FOR SAFETY-CRITICAL APPLICATIONS IN MEDICAL SYSTEMS

(75) Inventors: Scott A. Bielski, Sussex, WI (US); Matthew B. Peterson, Franklin, WI (US); Kevin A Coombs, Pewaukee, WI (US); Jonathan M. Butzine, Oconomowoc, WI (US); Kenneth M Stopar, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 908 days.

(21) Appl. No.: 11/556,152

(22) Filed: Nov. 2, 2006

(65) Prior Publication Data

US 2008/0130835 A1    Jun. 5, 2008

(51) Int. Cl.
*H05G 1/58*    (2006.01)

(52) U.S. Cl. ...................................................... 378/117
(58) Field of Classification Search ................. 378/117, 378/193–197, 204, 210
See application file for complete search history.

(56) References Cited

U.S. PATENT DOCUMENTS 7,177,393 B2 *    2/2007    Kanemitsu .................. 378/117

* cited by examiner

*Primary Examiner*—Courtney Thomas
(74) *Attorney, Agent, or Firm*—Peter Vogel, Esq.; William Baxter, Esq.; Michael G. Smith, Esq.

(57) ABSTRACT

Systems, methods and apparatus are provided through which a safety switch arrangement is assembled to prevent false activation of a subsystem in a medical system. In some embodiments, the safety switching arrangement comprises at least a first and a second type of switching element. In some embodiments, the first and the second type of switch each have an output that is processed by a processor, controller, or logic unit to produce an output signal for activating or deactivating a subsystem in the medical system.

20 Claims, 8 Drawing Sheets

REDUNDANT SWITCH MECHANISM FOR SAFETY-CRITICAL APPLICATIONS IN MEDICAL SYSTEMS

FIELD OF THE INVENTION

This invention relates generally to a safety switch arrangement for medical devices, and more particularly to dual switch arrangement for preventing false activation of subsystems in a medical system.

BACKGROUND OF THE INVENTION

In many medical systems, including medical imaging systems, the positioning sub-systems contain one or more motorized axes. A button on the operator console can invoke motion on these axes. This button represents a single point of failure that could result in harm to a patient or operator if a malfunction were to occur.

To circumvent this problem in existing equipment, the operator is required to depress two separate buttons, which is not necessarily the most failsafe or most ergonomically correct solution. For example, a dual-switch that uses two pressure-based switches could be tricked into activation if it was pressed too hard or if a heavy object was placed on it.

For the reasons stated above, and for other reasons stated below which would become apparent to those skilled in the art upon reading and understanding the present specification, there is a need in the art for a safety switch arrangement that is not prone to false activation. There is also a need for controlling subsystems in medical imaging devices through the use of switches incorporating different technologies.

BRIEF DESCRIPTION OF THE INVENTION

The above-mentioned shortcomings, disadvantages and problems are addressed herein, which will be understood by reading and studying the following specification.

In one aspect, an apparatus for preventing false activation of a subsystem in a medical system, the apparatus comprising: a switch arrangement having a first type of switch and a second type of switch, wherein each switch generates an 'on' state signal and an 'off' state signal; a controller coupled to the switch arrangement for controlling the subsystem based on the generated state signals from the first type and the second type of switch.

In another aspect, the first type of switch is a pressure based switch and the second type of switch is a non-pressure-based switch. Further, the second type of switch is positioned directly above, directly below, or in the immediate vicinity of the first type of switch.

In yet another aspect, the controller further comprises control logic operable to logically combine the generated state signals from the first type and the second type of switch; wherein the controller further comprises: control logic operable to convert and calibrate the generated state signals from the first type and the second type of switch.

In a further aspect, a system for controlling a subsystem in a medical system, the system comprising a first type of switch for generating an 'on' state signal and an 'off' state signal; a second type of switch abutting the first type of switch for generating an 'on' state signal and an 'off' state signal; and a processor coupled to the first type of switch and the second type of switch for controlling the subsystem based on the generated state signals from the first type and the second type of switch.

In still yet a further aspect, a method for safely switching a subsystem, in a medical system, by performing the action of receiving a first state signal from a first type of switch; receiving a second state signal from a second type of switch; processing the first state signal and the second state signal; and switching the subsystem based on the processed state signals from the first type and the second type of switch; wherein the second type of switch is adjacent to the first type of switch; wherein the state signal is an 'on' state signal and an 'off' state signal. Further, the method further performs the action of logically combining the received state signals from the first type and the second type of switch, and converting and calibrating the received state signals from the first type and the second type of switch.

Apparatus, systems, and methods of varying scope are described herein. In addition to the aspects and advantages described in this summary, further aspects and advantages will become apparent by reference to the drawings and by reading the detailed description that follows.

DETAILED DESCRIPTION OF THE INVENTION

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

System Level Overview

Figure 1:
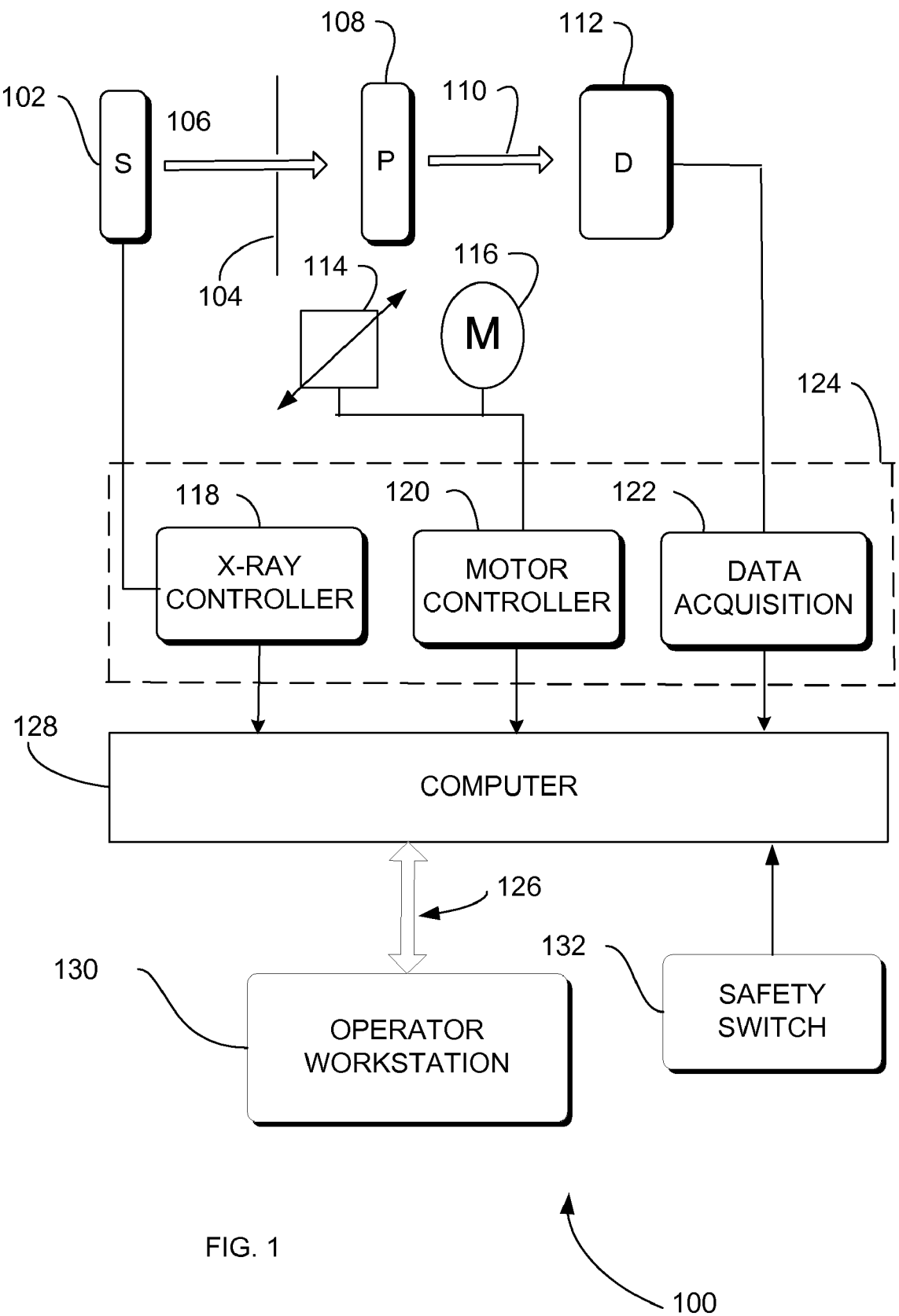
FIG. 1 is a diagram illustrating a system-level overview of an exemplary embodiment.

FIG. 1 is a block diagram that provides a system level overview. Embodiments are described as operating in a multi-processing, multi-threaded operating environment on a computer.

FIG. 1 illustrates diagrammatically an exemplary embodiment of a medical imaging system 100 for acquiring and processing image data. While the exemplary embodiment shows an X-ray imaging system 100, the system may be a computed tomography (CT)system, a positron emission tomography (PET) system, a magnetic resonance (MR) system, a nuclear medicine system, or any other medical system having safety-critical applications.

In the exemplary embodiment shown in FIG. 1, the medical imaging system 100 includes an X-ray source 102 positioned adjacent to a collimator 104. In this arrangement, the X-ray source 102 is typically an X-ray tube. Other modalities, however, possess different sources of imaging energy or radiation. For instance, modalities such as PET and nuclear medicine utilize an injectable radionucleotide as a source 102, and source 102 encompasses such alternative sources of imaging energy or radiation which are utilized in other types of imaging systems.

Returning to FIG. 1, the collimator 104 permits a stream of radiation 106 to pass into a region in which a subject, such as a human patient 108 is positioned. A portion of the radiation 110 passes through or around the subject and impacts a detector, represented generally at reference numeral 112.

The detector 112 produces electrical signals that represent the intensity of the incident X-ray beam 110. These signals are acquired and processed to reconstruct an image of the features within the subject. Source 102 is controlled by a system controller 124 which furnishes both power and control signals for examination sequences. Moreover, detector 112 is coupled to the system controller 124, which commands acquisition of the signals generated in the detector 112. The system controller 124 may also execute various signal processing and filtration functions, such as for initial adjustment of dynamic ranges, interleaving of digital image data, and so forth. In general, system controller 124 commands operation of the imaging system to execute examination protocols and to process acquired data. In the present context, system controller 124 also includes signal processing circuitry, typically based upon a general purpose or application-specific digital computer, associated memory circuitry for storing programs and routines executed by the computer, as well as configuration parameters and image data, interface circuits, and so forth.

In the arrangement illustrated in FIG. 1, system controller 124 is coupled to a linear positioning subsystem 114 and rotational subsystem 116. The rotational subsystem 116 enables the X-ray source 102, collimator 104 and the detector 112 to be rotated one or multiple turns around the region to be imaged. It should be noted that the rotational subsystem 116 might include a gantry suitably configured to receive the region to be imaged. Thus, the system controller 124 may be utilized to operate the gantry.

The linear positioning subsystem 114 enables the region to be imaged to be displaced linearly, allowing images to be generated of particular areas of the patient 108.

Additionally, as will be appreciated by those skilled in the art, the source of radiation 102 may be controlled by an X-ray controller 118 disposed within the system controller 124. Particularly, the X-ray controller 118 is configured to provide power and timing signals to the X-ray source 102. Those of ordinary skill in the art understand that the source 102, detector 112, and X-ray controller 118 comprise suitable analog circuitry for performing their operations.

A motor controller 120 is utilized to control the movement of the rotational subsystem 116 and the linear positioning subsystem 114. Further, the system controller 124 is also illustrated comprising a data acquisition system 122. In this arrangement, the detector 112 is coupled to the system controller 124, and more particularly to the data acquisition system 122. The data acquisition system 122 receives data collected by readout electronics of the detector 112. The data acquisition system 122 typically receives sampled analog signals from the detector 112 and coverts the data to digital signals for subsequent processing by a computer 128 through a data interchange device 126 such as a LAN, WAN, or Internet. The data acquisition 122 can be performed at the detector 122 level without departing from the concept of the invention.

The computer 128 is typically coupled to the system controller 124. The data collected by the data acquisition system 122 may be transmitted to the computer 128 and moreover, to a memory such as shown in 306, 308, 310 in FIG. 3. It should be understood that any type of memory to store a large amount of data may be utilized by such an exemplary system 100. Also the computer 128 is configured to receive commands and scanning parameters from an operator via an operator workstation 130 typically equipped with a keyboard and other input devices. An operator may control the system 100 via the input devices. Safety switch 132 is shown coupled to computer 128 so that the operator can activate or deactivate a subsystem in the medical imaging device. A subsystem is a grouping of items that perform a set of functions within a particular end product. In medical imaging it can be the X-ray source, the detector, the positioning hardware, motor system for position imaging equipment or imaging subject, or any other set of components that can be defined by a common objective or position within the overall imaging system 100. The safety switch 132 can be reserved for those subsystems that may pose the greatest harm to the patient 108. For example, it may be desirable to have confirmation that a human operator has pressed the safety switch and that the medical imaging system can start the imaging process. After the switch has been pressed the operator may observe the reconstructed image and other data relevant to the system from computer 128, initiate imaging, and so forth.

A display may also be coupled to the operator workstation 130 or computer 128 may be utilized to observe the reconstructed image and to control the imaging process. Additionally, the scanned image may also be printed on to a printer which may be coupled to the computer 128 and the operator workstation 130. Further, the operator workstation 130 may also be coupled to a picture archiving and communications system (PACS) through appropriately programmed ports. It should be noted that PACS may be coupled to a remote system, radiology department information system, and hospital information system or to an internal or external network, so that others at different locations may gain access to the image and to the image data.

It should be further noted that the computer 128 and operator workstation 130 may be coupled to other output devices which may include standard or special purpose computer monitors and associated processing circuitry. One or more operator workstations 130 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or, in an entirely different location, linked to the image acquisition system via one or more configurable networks, such as the Internet, virtual private networks, and so forth.

Figure 2:
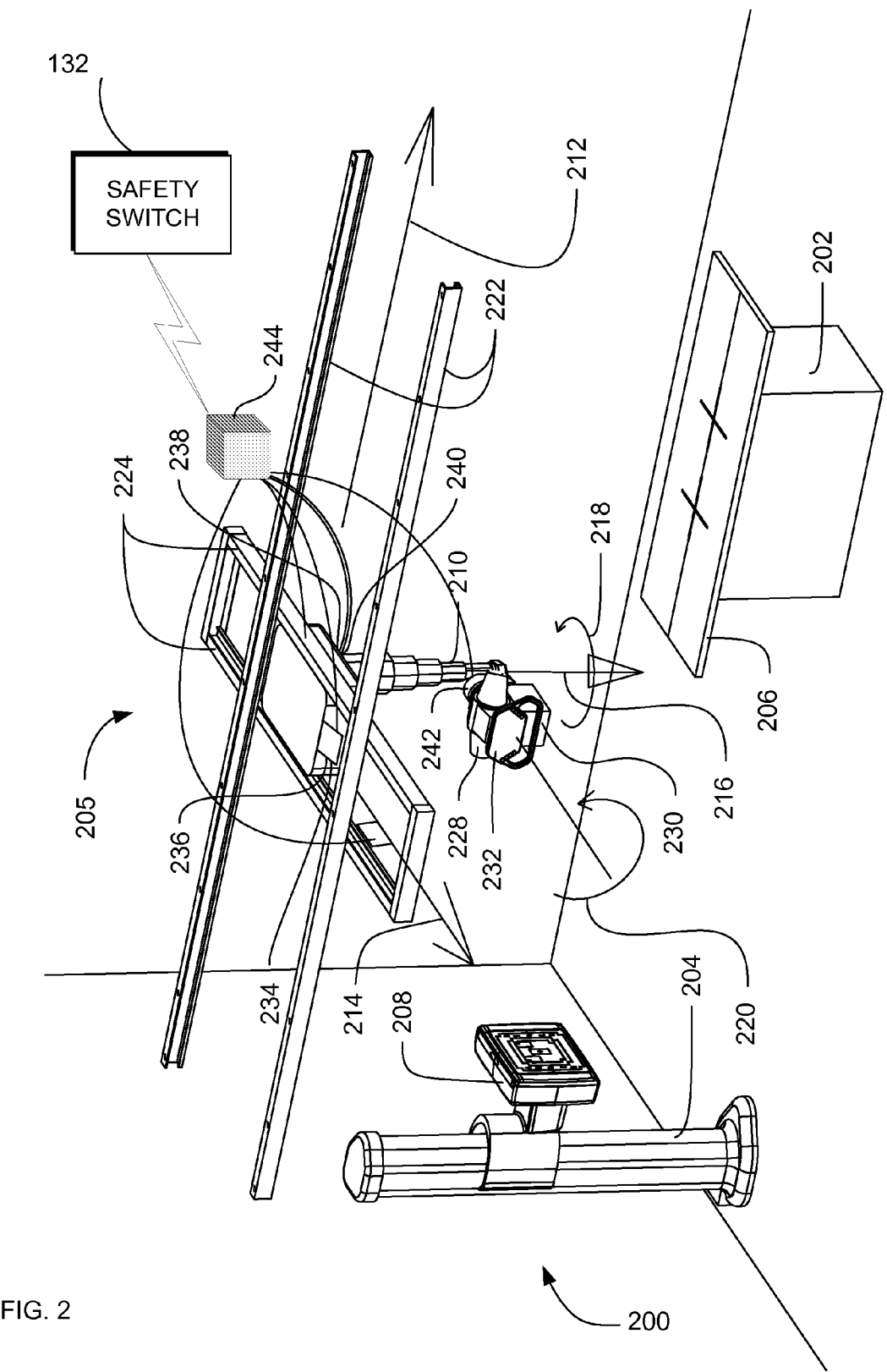
FIG. 2 is a diagram illustrating a system-level overview of another exemplary embodiment.

FIG. 2 is a diagram illustrating a system-level overview of an exemplary embodiment of a radiographic system 200. System 200 includes a radiographic table 202 and/or a radiographic wall stand 204, and a radiographic positioning system 205. The radiographic table 202 and the wall stand 204 each contain an image receptor, 206 and 208, respectively.

An overhead tube support (OTS) 210 for performing diagnostic imaging procedures is also included. The OTS 210 provides three linear motions (longitudinal X 212, lateral Y 214 and vertical Z 216) which are perpendicular to each other, and two rotational rotations (rotation about the vertical axis "a" 218, and rotation about one horizontal axis "b" 220).

Longitudinal positioning rails 222 are mounted to a ceiling (not shown). Lateral positioning rails 224 move along the longitudinal positioning rails 222 in the longitudinal X 212 motion. In other embodiments, the lateral positioning rails 224 are mounted to a ceiling and the longitudinal positioning rails 222 move along the lateral positioning rails 224 in the lateral Y 214 motion.

A carriage 226 moves along lateral positioning rails 224 in the lateral Y 214 motion. The OTS 210 is mounted on the carriage 226. A tube mount assembly 232 includes an X-ray source 228 and collimator 230. The tube mount assembly 232 is mounted to the OTS 210. The tube mount assembly 232 and/or the OTS 210 rotate about the vertical "a" 218 axis and the vertical "b" 220 axis.

The OTS 210 can be positioned at any attitude and position within the reaches of radiographic system 200. This flexibility in positioning is important in achieving alignment of the OTS 210 to an image receptor for imaging of a subject that is positioned on the radiographic table 202 or the radiographic wall stand 204. The alignment of the OTS 210 with an image receptor may be directed and/or controlled automatically by a control unit 244 or the alignment may be directed and/or controlled manually.

The lateral positioning rails 224 are operably coupled to the longitudinal positioning rails 122 through one or more first motorized drives 234. The carriage 226 is operably coupled to the lateral positioning rails 224 through one or more second motorized drives 236. In some embodiments, the OTS 210 is operably coupled to the carriage 226 through one or more third motorized drives 238 that rotates the OTS about the vertical Z 216. In some embodiments, the OTS 210 is also operably coupled to the carriage 226 through one or more fourth motorized drives 240 that extend the OTS along the vertical Z 216. In some embodiments, the X-ray source 228 is operably coupled to the OTS 210 through one or more fifth motorized drives 242 that rotate the X-ray source 128 about the horizontal axis "b" 220.

Each motorized drive includes a motor, and a position feedback measuring device, and in some embodiments a clutch and/or a lock or a brake. Each position feedback measuring device further includes a potentiometer, an encoder, a resolver, or a similar device. In the embodiments that lack a clutch, an efficient motor (having high quality bearings and high quality gears) is directly coupled, so that in manual motion the operator causes rotation of the motor armature as well as the OTS.

A control unit 244 is operably coupled to the one or more first motorized drives 234, the one or more second motorized drives 236, the one or more third motorized drives 238, the one or more fourth motorized drives 240 and the one or more fifth motorized drives 242. The control unit 244 controls operation of the motorized drives, which positions the X-ray source 228 and collimator 230 into alignment with a radiographic receptor 206 or 208. The safety switch can be directly connected through a dedicated line or wireless channel to the control unit 244 so as to allow activation or deactivation of the motorized drives.

In some implementations, more than one control unit 244 is included in system 200. Each control unit controls one or more motorized drives 234, 236, 238, 240 and/or 242. For example, in one implementation system 200 includes one control unit for each motorized drive. Each control unit communicates with the other control units, directly, or through other computers.

The control unit 244 improves the accuracy of positioning of the apparatus 228 and 230. The control unit 244 also maintains proper alignment of the apparatus 228 and 230 with the radiographic image receptors 206 and 208 over the full range of travel of the apparatus 228 and 230. The control unit 244 also provides an ability to correct for imperfections in geometry in the apparatus and to allow for greater tolerance in precision in manufacturing and installation. The control unit 244 also reduces confusion of the operator in the relationship between the function of the switches and the motion of the OTS because the positioning of the apparatus 228 and 230 is performed by the control unit 244.

The system level overview of the operation of an embodiment has been described in this section of the detailed description. A control unit 244 controls the motorized drives to position an X-ray source of apparatus 228 and a collimator of apparatus 230 into alignment with a radiographic receptor 206 or 208.

While the system 200 is not limited to any particular radiographic table 202, radiographic wall stand 204, image receptors 206 and 208, OTS 210, longitudinal positioning rails 222, lateral positioning rails 224, carriage 226, X-ray source 228, collimator 230, or control unit 244. For sake of clarity, a simplified radiographic table 202, radiographic wall stand 204, image receptors 206 and 208, OTS 210, longitudinal positioning rails 222, lateral positioning rails 224, carriage 226, X-ray source 228, collimator 230, and control unit 244 have been described.

Figure 3:
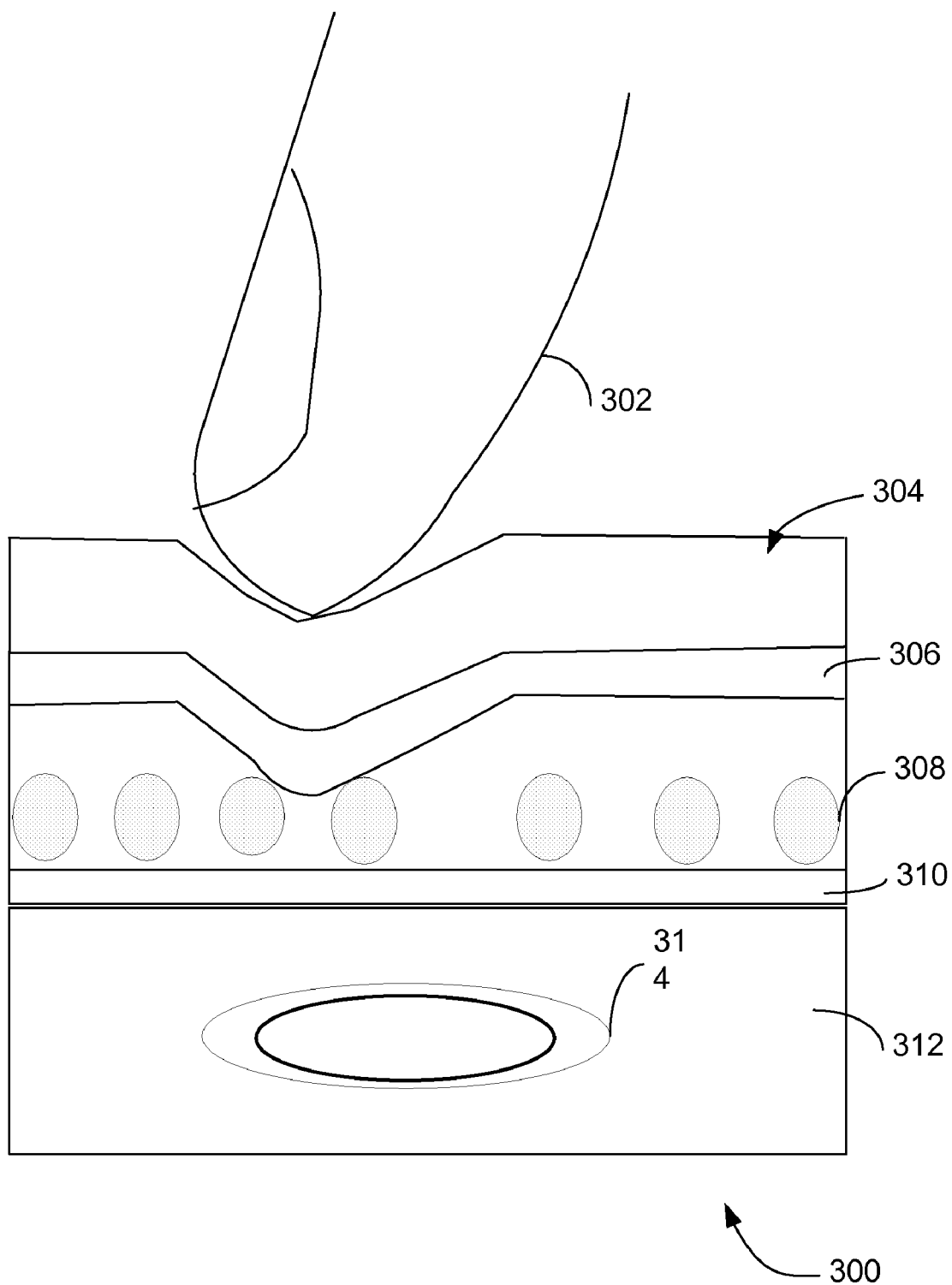
FIG. 3 is a diagram of a safety switch arrangement according to an embodiment showing elements of a first and second type of switch.

FIG. 3 is a representation of the elements of a safety switch according to an embodiment. The switch arrangement 300 solves the need in the art for a safety switch arrangement that is not prone to false activation. The switch arrangement 300 includes a first conductive layer 306 on a membrane 304 or flexible substrate, a second conductive layer 310 on a substrate 312, and a composite material disposed between the conductive layers, the composite material including conductive particles 308 separated by insulating material. Application of a touch force from a finger 302 or other object asserts a pressure on membrane 304 causing conductive layer 306 to move towards conductive layer 310. Upon application of sufficient force, electrical contact between conductive layers 306 and 310 can be achieved through one or more single particle contacts. As shown, electrical contact is made between the conductive layers via single particle contacts with particles 308. Removing the finger or other object allows membrane 304 and conductive layer 306 to return to a position where the conductive layers are again electrically isolated.

Positioned below conductive layer 310 is a sensing electrode 314 for detecting contact with membrane 304. The sensing electrode 314 is for all practical purposes a capacitor. When a grounded object (finger) is brought closer to the sensing electrode 314 there is a change in the capacitance of the sensing electrode 314. All objects have a free air capacitance when measured with reference to ground. Further, capacitors in parallel increase the capacitance of sensing electrode 314 while capacitors in series reduce the capacitance of sensing electrode 314. Therefore, when an object such as a finger approaches the membrane 304 the capacitance at sensing electrode 314 is increased.

Figure 4:
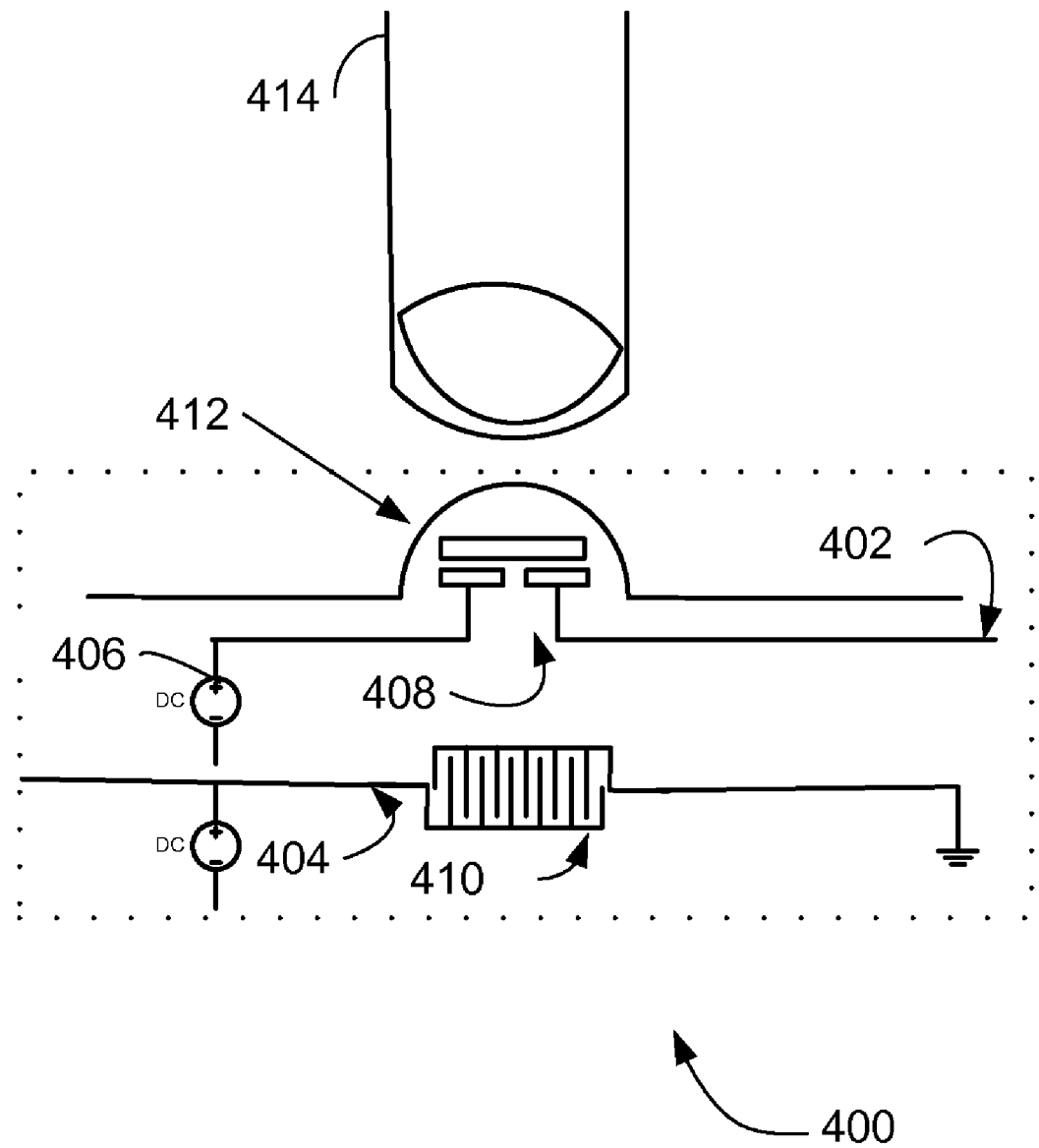
FIG. 4 is a diagram of a safety switch arrangement according to an embodiment showing a first and second type of switch.

FIG. 4 is a representation of a safety switch according to an embodiment. Switch arrangement 400 solves the need in the art for a safety switch arrangement that is not prone to false activation. The safety switch arrangement 400 includes a first type of switch 408 that can be, but is not limited to, an electromechanical switch, a strain gauge, a pressure sensitive resistor/sensor combination, a hall effect device/magnet combination, reed switch/magnet combination, a piezo element, or a capacitance sensor which detects the force applied to the membrane wall 412. Thus, the switch arrangement 400 may be adapted for a wide range of applications in a wide variety of mounting structures. While this embodiment is depicted as a rectangular conductive case, the invention contemplates cases of various shapes and sizes as well as a variety of installation means other than those depicted in FIG. 4. As noted in FIG. 3 the first type of switch 408 comprise a membrane wall 412, conductors (306,310), and contacts 308 for determining activation. The second type of switch 410 comprises a sensing electrode 314 whose capacitance changes when brought into contact with a grounded object such as a finger 414. An applied pressure to membrane wall 412 causes membrane wall 412 to deflect and causes the first type of switch 408 to output response signal 402. The response signal 402 is proportional to the force applied by finger 414. In operation when a finger 414 or any other object is placed on membrane wall 412 a force is applied on contact 306 causing it to form a path through 308 and 310 for current to flow. Thus, response signal 402 has a range that can span an "OFF" state, zero voltage or absence of a voltage, or an "ON" state, full voltage or a reference voltage.

The second switch is a non-pressure-based switch such as a capacitive, e-field, or inductive switch. Like the first type of switch, the second type of switch produces a response signal that spans the range of "OFF" and "ON" states based on the intensity of the activation. As noted earlier the first type of switch 408 is pressure activated and the response signal 402 is proportional to the applied force. The second type of switch 410 is proximity activated and the second response signal 404 is proportional to the proximity of the object 414 to the second type of switch 410. When the finger 414 contacts membrane wall 412, a sensing electrode 410 detects the contact. The sensing electrode 410 is part of a capacitive sensor and typically has a guard and sensing plate (not shown). When the finger 414 is brought closer to the sensing electrode 414, the capacitance of the sensing plate is changed. The change in capacitance leads to a change in the voltage produced at output 404. The second switch 410 can be placed directly below, above, or near the first switch. It should be noted that based on the configuration different calibrations, compensations, or signal conditioning is required to account for the activation of either switch.

In combination the first switch 408 and the second switch 410 produce a switch arrangement 400 that can be used to prevent false activation of a subsystem or any element of a medical imaging device. The operator is thus only required to activate a single switch, and is most likely unaware that the two-switch mechanism is in use. The invention allows for a more comprehensive failsafe mechanism than existing single-switch implementations. One safety advantage is redundancy, if either switch (408, 410) fails in the activated state ("ON" state), the other switch prevents a false activation. An additional safety advantage is that this implementation is not as easily foiled as a single-switch implementation, or a dual-switch implementation that uses common technology for both switches. For example, a dual-switch that used two pressure-based switches (408) could be tricked into activation if a heavy object was placed on it. In the case of a dual switch (capacitive or E-field) non-pressure (410), the operator must apply the appropriate minimum pressure, as well as the appropriate dielectric constant (i.e., change in capacitance or voltage) to activate the switch arrangement.

Figure 5:
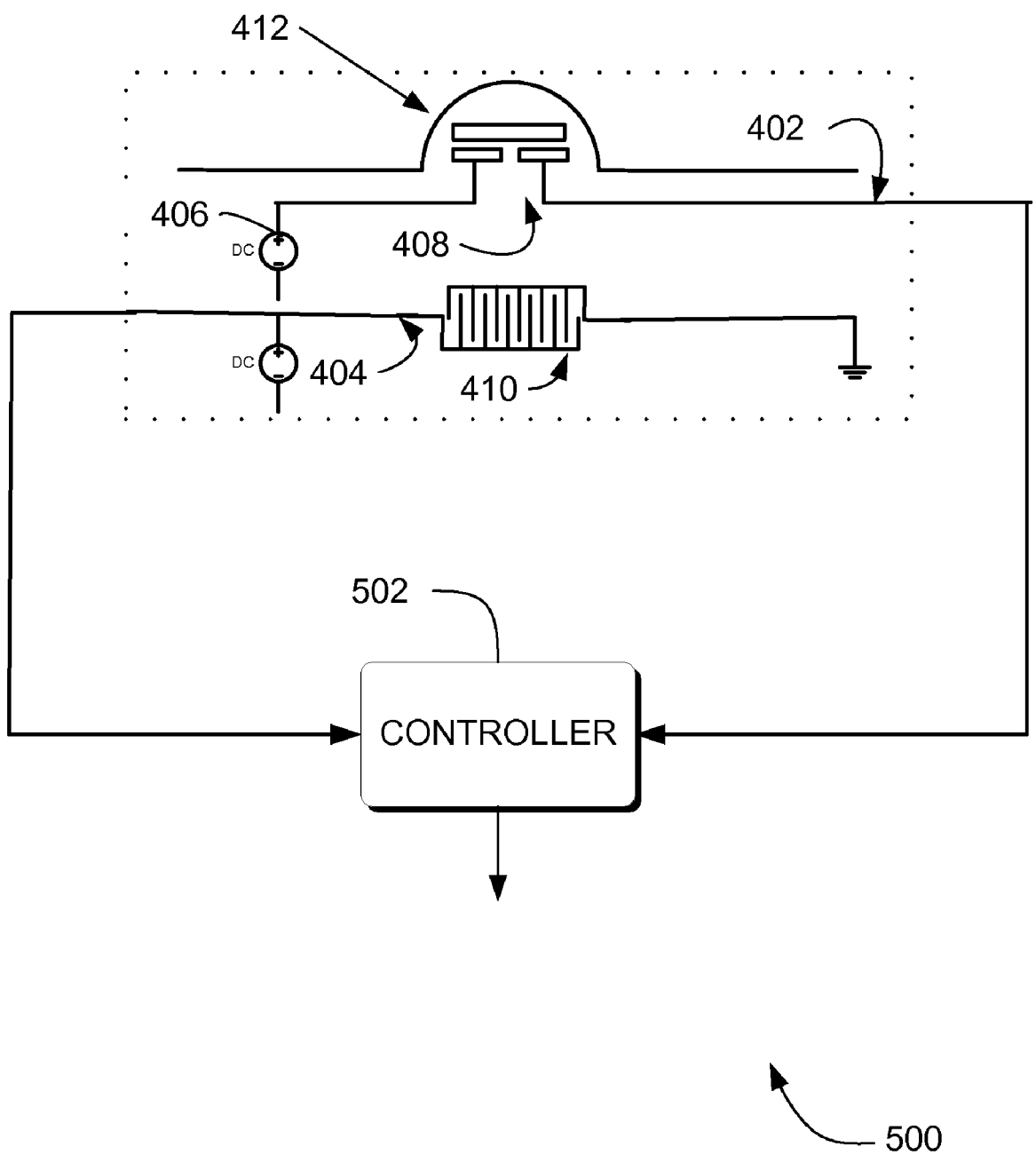
FIG. 5 is a diagram of a safety switch arrangement according to an embodiment showing a first and second type of switch and a controller.

FIG. 5 is a schematic diagram of an application of the switch arrangement 400 to the generation of a control signal by a controller 502. An appropriate force applied at membrane 412 causes a signal to be generated at output 402. The output is received by controller 502 and with appropriate logic the signal is filtered to generate an indication of an "ON" state or an "OFF" state from the first switch. In critical application it may be desirable to know that an operator is pressing the switch, that the first type of switch has not failed, or that a certain threshold force has been exceeded. The addition of a non-pressure switch (second switch) would be able to answer all these applications. As to application of an operator pressing the switch when the finger 414 touching the front panel 412, the capacitor in switch 410 changes causing a variation in voltage at output at 404. The failure of a switch can be monitored by state shown by the other switch. For example, if the first type of switch does not registered but the second type of switch shows that a finger is pressing against the membrane 412 one could infer that the first switch is no longer operating. The exceedance of a minimum force can be accomplished by measuring the pressure variations at the first switch or the voltage/capacitance variations at the second switch 410. The controller 502 after performing logical operations such as combining the signals can generate a control signal to the drivers to activate or deactivate the subsystem in the medical imaging device.

Figure 6:
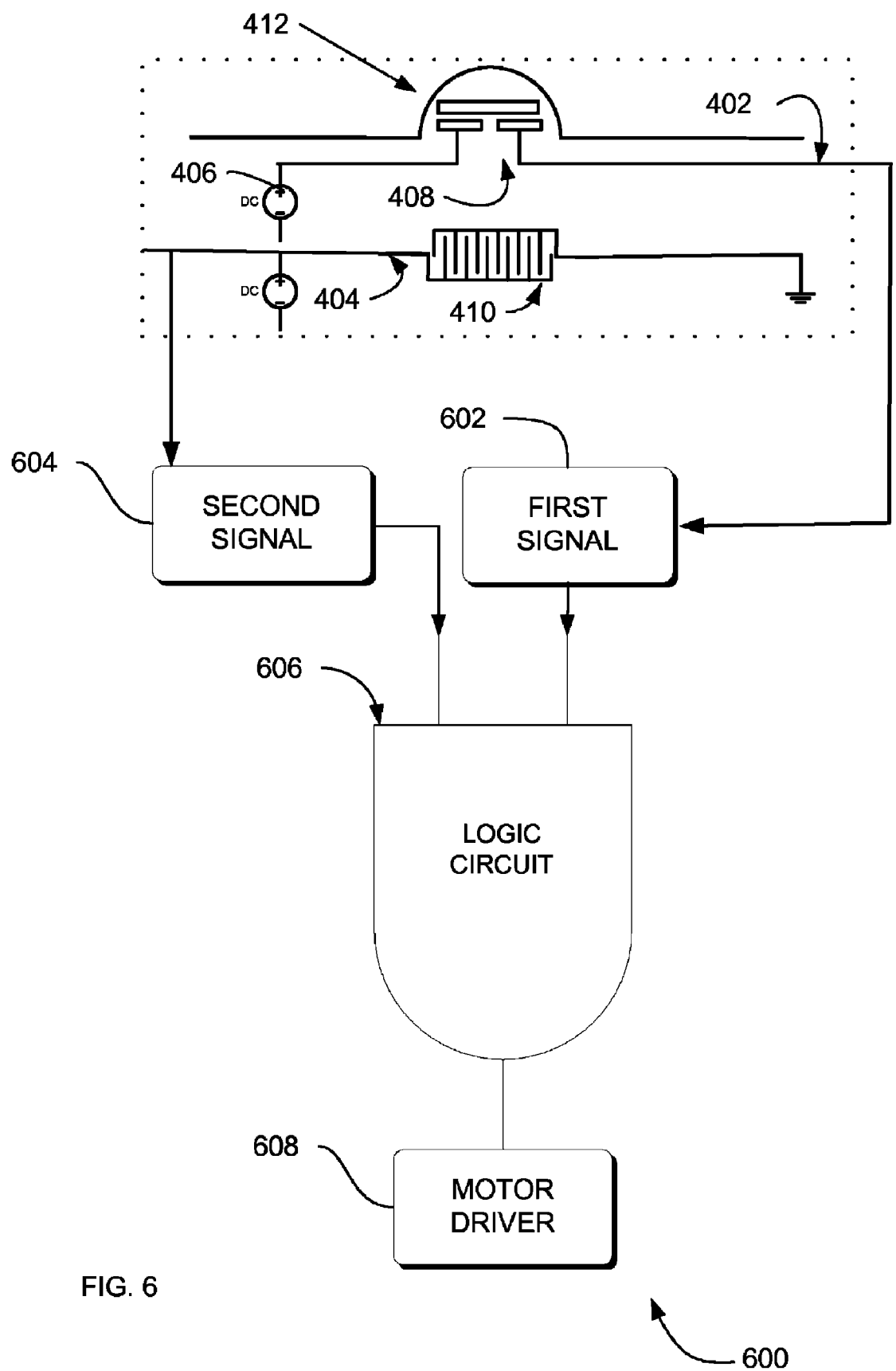
FIG. 6 is a diagram of an apparatus according to an embodiment showing a first and second type of switch for controlling a motor driver.

FIG. 6 is a schematic diagram of an application of the switch arrangement 400 to the generation of a control signal by a logic unit 606 after being processed by devices 602 and 604. The logic unit 606 is any device that can accept two inputs and render a decision as to the level of the output. Examples of logic unit 606 can be an and gate, or gate, exclusive or gate, or a combination of these gates. When used as an "and gate" both the first and second signals must indicate an "ON" state before the motor driver 608 is activated. The first signal 602 and the second signal 604 have to be calibrated to get an indication as to the state of the signals at each switch. With the appropriate design or with the appropriate selection circuits 602 and 604 can be picked to trigger at a desired level. Circuit 602 could be designed with a trigger level that is correlated to the lowest pressure or force needed to trigger an "on" state. Likewise, circuit 604 could be designed with a desired distance from the switch arrangement before an "ON" state is registered at logic unit. Circuits 602 and 604 could be Schmitt Trigger Circuits (STC) due to the STC's ability to quickly detect voltage levels.

Figure 7:
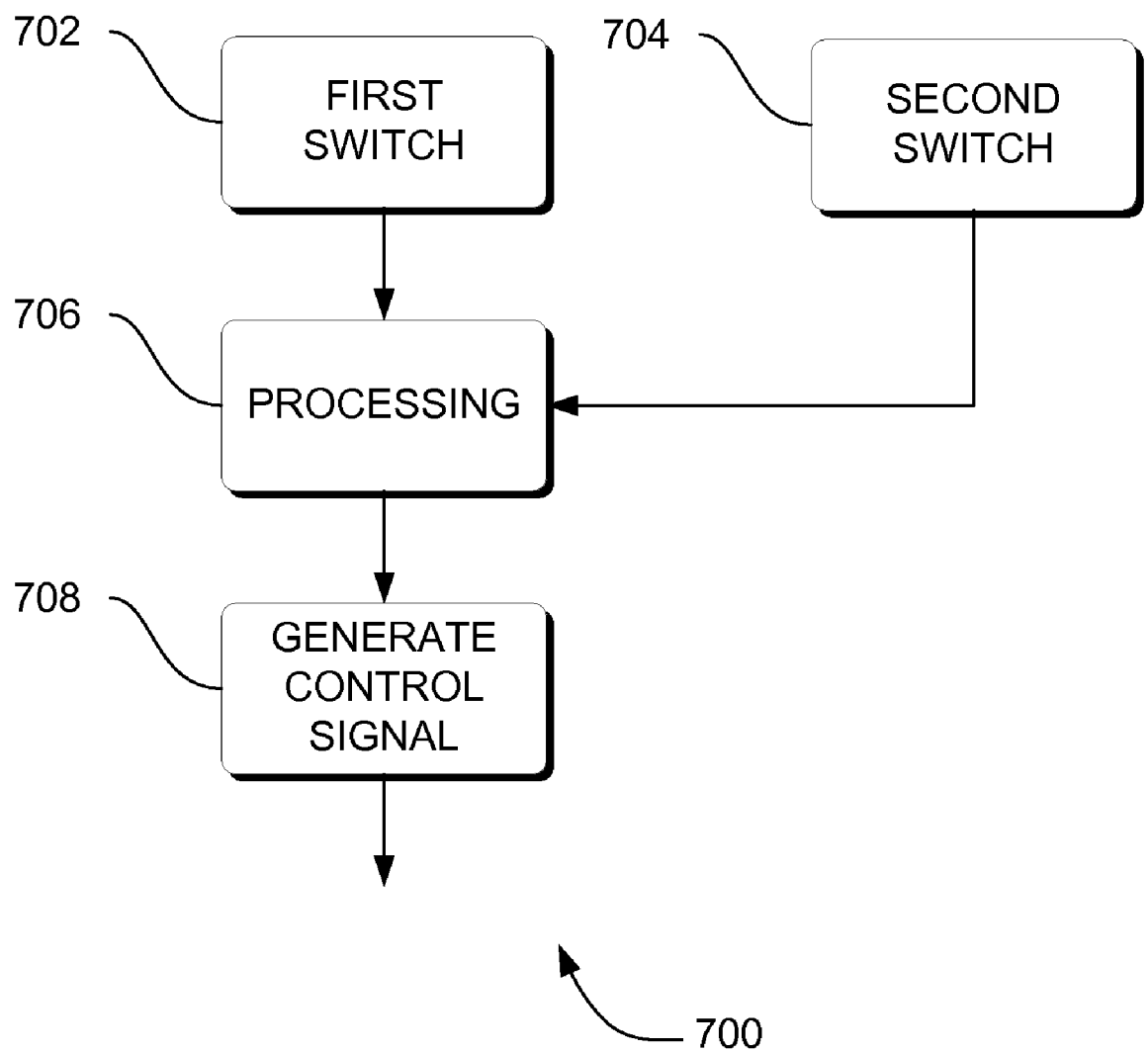
FIG. 7 is a flowchart of a method, according to an embodiment for generating a control signal from processed signals from the first and second type of switch.

FIG. 7 is a flowchart of a method 700 for safely switching a subsystem in a medical imaging system according to an embodiment. Method 700 solves the need in the art for a safety switch arrangement that is not prone to false activation.

Method 700 begins with action 702 when a force is applied to a first type of switch. The force could be from a user using an object or using a part pf the user's body. As noted earlier the signal from the first switch is proportional to the applied force at the switch. In action 704 a measurement of the change in characteristics of the second type of switch 704 will determined if the user is applying the force with an object or using a part of the user's body. For example, when the second switch is a capacitance switch we can measure the change in dielectric or the change in capacitance at the switch to register the state of the switch.

In the action 706, a processing of the signals is performed. The processing is inclusive of signal conditioning, signal conversion, calibration, or any other operation that could be performed by a digital signal processor (DSP). The signal from the first type of switch 702 could be set to a voltage level that exceeds an applied force or pressure. If the object being sensed, such as the finger 414, is an infinite distance from the sensor 410 then the switch is open (or turned "off"), the frequency output will be at its highest, or its lowest level because the capacitance based on the configuration would be either low or high. When the object being sensed, such as the finger 414, is at a finite distance (close) from the sensor 410 then the switch is close (or turned "on"), which is equivalent to a finger touching membrane 412, the change in capacitance at 410 solely determines the capacitance and the corresponding change in frequency. The processed signals are forwarded to action 708 for further processing.

In action 708, a control signal is generated. Based on the desired configuration a signal is generated to control the subsystem in the medical imaging device. When the configuration is that a given pressure is exceeded and a finger (user's body) is doing the pressing of the membrane a subsystem is activated. In such a configuration, a pressure with an object (pencil, pen, rod, etcetera) will not cause activation because the capacitance in that case will register an "OFF" state.

Figure 8:
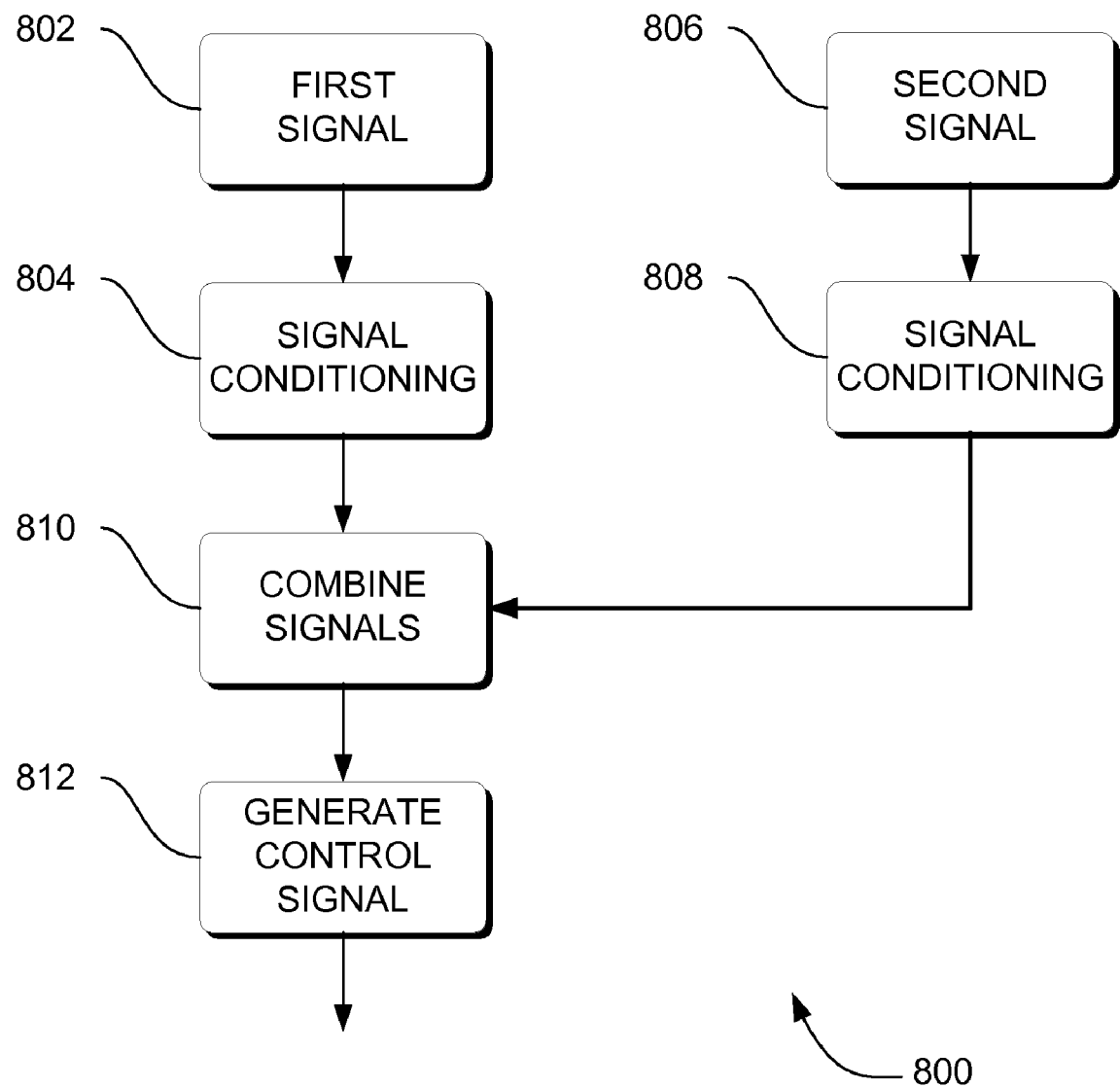
FIG. 8 is a flowchart of a method, according to an embodiment for generating a control signal from combined signals from the first and second type of switch.

FIG. 8 is a flowchart of a method 800 for safely switching a subsystem in a medical imaging system according to an embodiment. Method 800 solves the need in the art for a safety switch arrangement that is not prone to false activation.

Method 800 includes a first signal 802 from a first type of switch, a second signal 806 from a second type of switch, signal conditioning (804, 808), a combiner for the signals, a generation of a control signal based on the combine signals.

In action 802 a first signal from a first type of switch is received. The signal is then processed or conditioned at 804 to provide the appropriate conversion and calibration. Actions 806 and 808 perform the same procedures fro the second signal from the second type of switch.

In action 810 the conditioned signals (804, 808) are combined to generate an input so action 812 can issue a control signal. The combination as noted earlier depends on the objective of the designed. If the objective is no activation until a first signal and a second signals are received then the combined signal will be an "AND" statement. If the objective is for other purposes then registration that both switches are selected then a combination could be "OR" gate, exclusive "OR" gate, or any other arrangement.

Once the signals have been combined in action 810 a control signal is generated at action 812 to control the subsystem in the medical imaging device.

In some embodiments, methods 700-800 are implemented as a computer data signal embodied in a carrier wave, that represents a sequence of instructions which, when executed by a processor, such as processor 304 in FIG. 3, cause the processor to perform the respective method. In other embodiments, methods 700-800 are implemented as a computer-accessible medium having executable instructions capable of directing a processor, such as processor 304 in FIG. 3, to perform the respective method. In varying embodiments, the medium is a magnetic medium, an electronic medium, or an optical medium.

A switch arrangement for activating/deactivating a subsystem in a medical imaging device is described. Although specific embodiments are illustrated and described herein, it will be appreciated by those of ordinary skill in the art that any arrangement which is calculated to achieve the same purpose may be substituted for the specific embodiments shown. This application is intended to cover any adaptations or variations.

In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments.

We claim:

1. An apparatus for preventing false activation of a subsystem in a medical system, the apparatus comprising:

a switch arrangement having a first switch and a second switch, wherein each switch generates a state signal ranging between 'off' and 'on', wherein the second switch comprises a sensing electrode whose capacitance changes when brought into contact with a grounded object and wherein a pressure applied to a membrane wall of the second switch causes the membrane wall to deflect and causes the first switch to output a response signal, the response signal being proportional to the applied force, wherein a force applied to the membrane causes the membrane to form a path through a memory for current to flow; and a controller coupled to the switch arrangement for controlling the subsystem based on the generated state signals from the first switch and the second switch.

2. The apparatus of claim 1, wherein the first switch further comprises a pressure based switch.

3. The apparatus of claim 1, wherein the second switch further comprises a non-pressure based switch.

4. The apparatus of claim 1, wherein the second switch is positioned directly above, directly below, or in the immediate vicinity of the first switch.

5. The apparatus of claim 1, wherein the medical system is a medical imaging system having an imaging source and an imaging detector; wherein the imaging source and the imaging detector are mounted independently of each other;

wherein the subsystem further comprises a motor drive for positioning the subsystem;

wherein the controller adjusts the position of the subsystem by controlling the motor drive.

6. The apparatus of claim 5, wherein the controller further comprises: control logic operable to:

logically combine the generated state signals from the first switch and the second switch.

7. The apparatus of claim 5, wherein the controller further comprises: control logic operable to:

convert and calibrate the generated state signals from the first switch and the second switch.

8. A system for controlling a subsystem in a medical system, the system comprising:

a first switch for generating a state signal ranging between 'off' and 'on';

a second switch abutting the first switch for generating a state signal ranging between 'off' and 'on'; wherein a pressure applied to a membrane wall of the second switch causes the membrane wall to deflect and cause the first switch to generate the 'on' state signal and a processor coupled to the first switch and the second switch for controlling the subsystem based on the generated state signals from the first switch and the second switch.

9. The system of claim 8, wherein the first switch further comprises a pressure based switch.

10. The system of claim 8, wherein the second switch further comprises a non-pressure-based switch.

11. The system of claim 8, wherein the second switch is positioned directly above, directly below, or in the immediate vicinity of the first switch.

12. The system of claim 8, wherein the medical system is a medical imaging system having an imaging source and an imaging detector; wherein the imaging source and the imaging detector are mounted independently of each other;

wherein the subsystem further comprises a motor drive for positioning the subsystem;

wherein the processor operates on the motor drive to adjust the position of the subsystem by controlling the motor drive.

13. The system of claim 12, wherein the controller further comprises control logic operable to perform:

convert and calibrate the generated state signals from the first switch and the second switch; and, logically combine the generated state signals from the first switch and the second switch.

14. A method for safely switching a subsystem in a medical system, the method comprising:

receiving a first state signal from a first switch, wherein a pressure applied to a membrane wall of a second switch causes the membrane wall to deflect and cause the first switch to generate an 'on' state signal;

receiving a second state signal from the second switch;

processing the first state signal and the second state signal; and switching the subsystem based on the processed state signals from the first switch and the second switch;

wherein the second switch is adjacent to the first switch;

wherein the state signals range between 'off' and the 'on'.

15. The method of claim 14, wherein the first switch further comprises a pressure based switch.

16. The method of claim 14, wherein the second switch further comprises a non-pressure-based switch.

17. The method of claim 14, wherein the second switch is positioned directly above, directly below, or in the immediate vicinity of the first switch.

18. The method of claim 14, wherein the medical system is a medical imaging system having an imaging source and an imaging detector; wherein the imaging source and the imaging detector are mounted independently of each other;

wherein the subsystem further comprises a motor drive for positioning the subsystem;

wherein the processing further includes adjusting the position of the subsystem by controlling the motor drive.

19. The method of claim 18, the method further comprising:

logically combining the received state signals from the first switch and the second switch.

20. The method of claim 18, the method further comprising:

converting and calibrating the received state signals from the first switch and the second switch.

\* \* \* \* \*